United States Patent
Li et al.

(10) Patent No.: US 10,377,699 B2
(45) Date of Patent: Aug. 13, 2019

(54) DAPTOMYCIN ANALOGUES AND A METHOD FOR THE PREPARATION OF DAPTOMYCIN OR A DAPTOMYCIN ANALOGUE

(71) Applicant: THE UNIVERSITY OF HONG KONG, Hong Kong (CN)

(72) Inventors: Xuechen Li, Hong Kong (CN); Hiu Yung Lam, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 167 days.

(21) Appl. No.: 14/073,399

(22) Filed: Nov. 6, 2013

(65) Prior Publication Data
US 2015/0126707 A1    May 7, 2015

(51) Int. Cl.
C07K 7/50     (2006.01)
C07C 227/18   (2006.01)
C07K 7/08     (2006.01)

(52) U.S. Cl.
CPC .............. *C07C 227/18* (2013.01); *C07K 7/08* (2013.01)

(58) Field of Classification Search
None
See application file for complete search history.

(56) References Cited

U.S. PATENT DOCUMENTS

| | | | | |
|---|---|---|---|---|
| 6,767,718 B2 * | 7/2004 | Leese | ............... | C07K 11/02 435/68.1 |
| 2003/0224475 A1 * | 12/2003 | Leese | ............... | C07K 11/02 435/68.1 |
| 2010/0184649 A1 * | 7/2010 | Metcalf, III | ............ | C07K 7/54 514/2.9 |

FOREIGN PATENT DOCUMENTS

| | | | | |
|---|---|---|---|---|
| CN | 101696235 | * | 4/2010 | |
| WO | WO/02/059322 | * | 8/2002 | ............ C12N 15/52 |
| WO | WO 02/059322 | * | 8/2002 | ............ C12N 15/52 |
| WO | WO2011/089215 | * | 7/2011 | |

OTHER PUBLICATIONS

Wong et al., Org. Biomol. Chem. (2013) 11, 7616.*
Gu et al., J Nat Prod (2007) 70(2), 233-40.*
Baltz, Methods in Enzymology (2009) 458, 511-531.*
Huber, Biotechnology Letters (1990) 12(11) 789-792.*
CN101696235translation (retrieved from http://www.google.com/patents/CN101696235A?cl=en on Dec. 11, 2017, 11 pages) (Year: 2010).*
BBC Covalent bonding (retrieved from http://www.bbc.co.uk/schools/gcsebitesize/science/add_aqa_pre_2011/atomic/covalentrev1.shtml on Dec. 12, 2017, 2 pages. (Year: 2017).*
Baltz et al. ('Natural products to drugs: daptomycin and related lipopeptide antibiotics' Natural Product Reports v22 2005 pp. 717-741). (Year: 2005).*
Grunewald et al. ('Synthesis and derivitization of daptomycin: a chemoenzymatic route to acidic lipopeptide antibiotics' JACS v126 2004 pp. 17025-17031) (Year: 2004).*
Grunewald supporting information (retrieved from http://pubs.acs.org/doi/suppl/10.1021/ja045455t/suppl_file/ja045455tsi20040920_073930.pdf on Dec. 12, 2017, pp. S1-S6) (Year: 2004).*
Bionda et al. ('Cyclic lipodepsipeptides: a new class of antibacterial agents in the battle against resistant bacteria' Future Med Chem v5(11) Jul. 2013 pp. 1-41) (Year: 2013).*
TranslatedCN 101696235 (retrieved from http://translationportal.epo.org/emtp/translate/?ACTION=description-retrieval&COUNTRY=CN&ENGINE=google&FORMAT=docdb&KIND=A&LOCALE=enEP&NUMBER=101696235&OPS=ops.epo.org/3.2&SRCLANG=zh&TRGLANG=en on Mar. 14, 2019, 22 pages) (Year: 2019).*
Ball, L-J. et al., "NMR structure determination and calcium binding effects of lipopeptide antibiotic daptomycin," *Org. Biomol. Chem.*, 2004, pp. 1872-1978, vol. 2.
Debono, M. et al., "A Complex of New Acidic Peptide Antibiotics: Isolation, Chemistry, and Mass Spectral Structure Elucidation", *The Journal of Antibiotics*, 1987, pp. 761-777, vol. 40, No. 6.
Lam, H. Y. et al., "Total Synthesis of Daptomycin by Cyclization via a Chemoselective Serine Ligation", *J. Am. Chem. Soc.*, 2013, pp. 6272-6279, vol. 135.
Milne, C. et al. "Biosynthesis of the (2S,3R)-3-Methyl Glutamate Residue of Nonribosomal Lipopeptides", *J. Am. Chem. Soc.*, 2006, pp. 11250-11259, vol. 128.
Qiu, J. et al., "Estimated pKa Values for Specific Amino Acid Residues in Daptomycin," *Journal of Pharmaceutical Sciences*, Oct. 2011, pp. 4225-4233, vol. 100, No. 10.

* cited by examiner

*Primary Examiner* — Karlheinz R. Skowronek
*Assistant Examiner* — Ronald T Niebauer
(74) *Attorney, Agent, or Firm* — Saliwanchik, Lloyd & Eisenschenk

(57) ABSTRACT

A method for the synthesis of daptomycin or a daptomycin analog is carried out on a resin to form a linear precursor followed by a serine ligation macrocyclization in solution. Daptomycin analogs can differ from daptomycin by substitution of amino acids residues and/or deletion or addition of amino acid residues. Daptomycin analogs can include a different fatty acid in the side arm of the daptomycin analog.

4 Claims, 6 Drawing Sheets

DAPTOMYCIN ANALOGUES AND A METHOD FOR THE PREPARATION OF DAPTOMYCIN OR A DAPTOMYCIN ANALOGUE

BACKGROUND OF INVENTION

The emergence of multi-drug resistant bacterial pathogens has created an urgent need for development of effective antibiotics that display new modes of action against resistant strains. Daptomycin is a lipodepsipeptide that is isolated from *Streptomyces roseoporus* obtained from soil samples from Mount Ararat (Turkey). Daptomycin is the first natural product antibiotic launched in a generation and is FDA approved for the treatment of skin infections caused by Gram-positive pathogens. Daptomycin has potent bactericidal activity with a unique mode of action against antibiotic-resistant Gram-positive pathogens, including methicillin-resistant *Staphylococcus aureus* (MRSA), vancomycin-resistant enterococci (VRE) and vancomycin-resistant *S. aureus*. Daptomycin undergoes a conformational change on binding to calcium ions to enable insertion into bacterial membranes and induce membrane leakage as the apparent mode of activity. Drug-resistance to daptomycin in pathogenic bacteria has not been observed. Daptomycin, as shown in FIG. 1, is a 13-amino acid cyclic lipodepsipeptide of the nonribosomal peptide family, as disclosed in Debono et al., *J. Antibiotics* 1987, 40, 761-777. It consists of a 31-membered ring of 10 amino acids and a linear 3-amino acid side-chain modified with an n-decanoyl lipid at the N-terminus. There are two unnatural amino acids, kynurenine (Kyn) and 3-methyl-glutamic acid (3-mGlu) within the sequence, along with D-Asn, D-Ser, and D-Ala.

Daptomycin's distinct mechanism of action is a new structural motif for the development of antibiotics. Only a few daptomycin analogues have been produced from biosynthesis, and these include mutations at D-Asn, D-Ser, 3-mGlu and Kyn via genetic engineering of the nonribosomal peptide synthetase (NRPS) in the daptomycin biosynthetic pathway. Chemo-enzymatic synthesis and semi-synthesis has resulted in modifications to the lipid chain and the δ-amino group of ornithine. The presence of two non-proteinogenic amino acids, Kyn and 3-mGlu, in the cyclic peptide backbone, and the macrolactamization of a 31-membered depsipeptidic ring render daptomycin a challenging target for total synthesis.

To this end an efficient synthetic method to daptomycin, that allows the assembly of the peptide sequence with precision and flexibility can allow a wide variation of daptomycin analogues for the establishment of the structure-activity relationship of daptomycin and the preparation of effective analogues thereof.

BRIEF SUMMARY

Embodiments of the invention are directed to a method for the syntheses of daptomycin molecules and to analogues thereof. Linear peptides are synthesized by solid phase peptide synthesis (SPPS) in combination with solution phase synthesis. Macrocyclization involves intramolecular Serine/Threonine ligation (STL) at the serine site of the sequence. Kynurenine residues are formed from by ozonolysis of tryptophan residues within an intermediate sequence.

DETAILED DISCLOSURE

Figure 1:
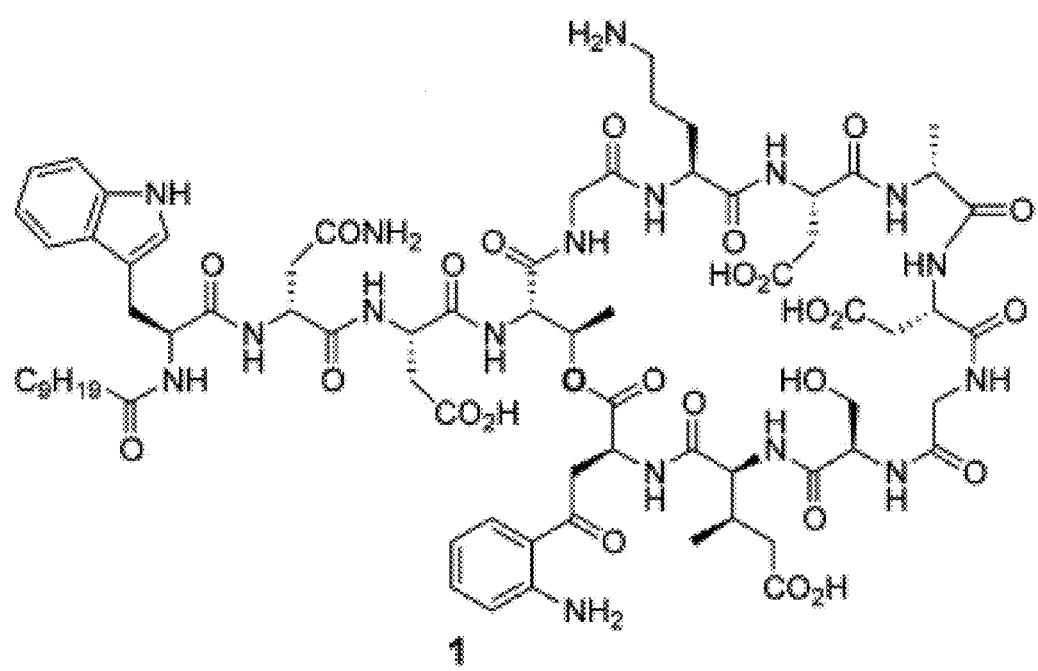
FIG. 1 shows the structure of daptomycin (1).

Embodiments of the invention are directed to daptomycin analogues and a method to prepare daptomycin or daptomycin analogues. In an embodiment of the invention, daptomycin or an analogue thereof is prepared by a series of reactions on a bound resin to form a linear precursor to the 31-membered cyclic peptide of daptomycin, or a 25 to 37-membered cyclic peptide of a daptomycin analogue, followed by macrocyclization of the linear precursor after detachment from the resin by a serine ligation. The preparation of the linear precursor involves a standard Fmoc solid phase peptide synthesis (Fmoc-SPPS) that is modified such that a trityl-resin-linked pentapeptide for daptomycin, or a tetrapeptide, pentapeptide or hexapeptide for a daptomycin analogue, is assembled that undergoes a HATU coupling with a N-terminal azide substituted tetrapeptide comprising the protected unnatural amino acid Kynurenine (Kyn) followed by: additional couplings with two amino acids for daptomycin or one to three amino acids for a daptomycin analogue under standard SPPS conditions where the last of the amino acids is serine; reduction of the azide; and additional homologation via Fmoc-SPPS to include two amino acids and a fatty acid for daptomycin, or one to three amino acids and a fatty acid for a daptomycin analogue to form a fatty acid terminal side arm of the linear precursor with a terminal N-protected serine. Upon release from the resin, the linear precursor's C-terminus is converted to a salicylaldehyde ester, or equivalent aldehyde ester, followed by: deprotection of the serine; deprotection of other protected functionality of the linear precursor; macrocyclization via formation of an N,O-acetal; and hydrolysis of the acetal to form daptomycin or a daptomycin analogue.

According to an embodiment of the invention, daptomycin analogues can have the structure:

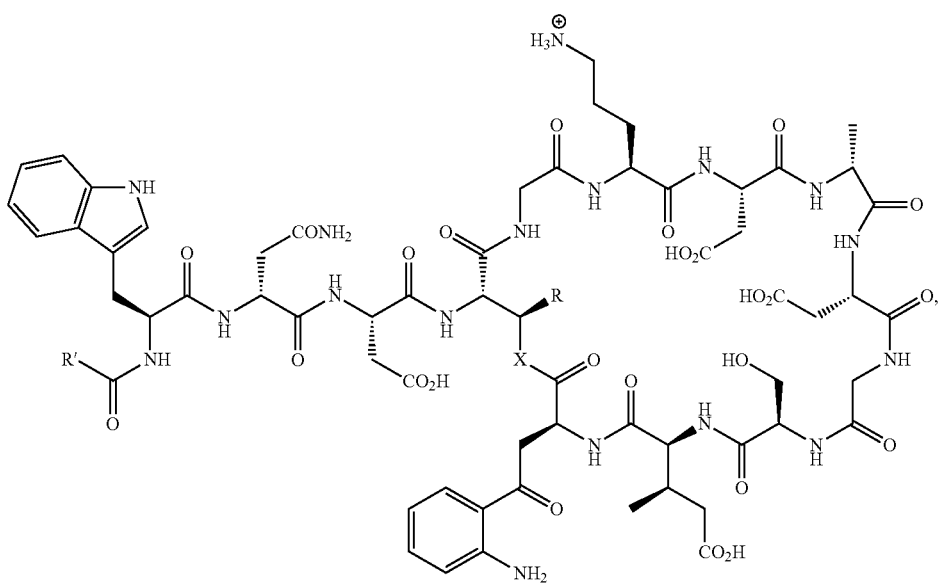

where X is O, NH, or S, R is H, $CH_3$, $C_2H_5$, $C_3H_7$, or $C_4H_9$, where R' is a $C_6$ to $C_{29}$ saturated or unsaturated hydrocarbon, and when X is O, R is not $CH_3$ or R' is $C_9H_{18}$. In an embodiment of the invention, any of the amino acid residues other than those from serine and the $H_2NCH(CHRXH)$ $CO_2H$ amino acid, can be deleted or substituted by another amino acid to yield analogue 2. The $H_2NCH(CHRXH)$ $CO_2H$ amino acid can be threonine, as in daptomycin, or it can be serine, R-3-hydroxy-S,2-aminopropanoic acid, R-3-hydroxy-S-2-aminobutanoic acid, R-3-hydroxy-S-2-aminopentanoic acid, cysteine, thiothreonine, R-3-thio-S-2-aminobutanoic acid, R-3-thio-S-2-aminopentanoic acid, S,R-2,3-diaminoproprionic acid, S,R-2,3-diaminobutanoic acid, or S,R-2,3-diaminopentanoic acid. In an embodiment of the invention, an additional amino acid can be included in the macrocycle or in the fatty acid terminal side-arm extending from the macrocycle. In an embodiment of the invention R'C(O)NH is a $C_7$ to $C_{26}$ saturated fatty acid amide or an unsaturated fatty acid amide, for example, any amide of enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, myristoleic acid, palmitoleic acid, sapienic acid, oleic acid, elaidic acid, vaccenic acid, linoleic acid, linolelaidic acid, α-linolenic acid, arachidonic acid, eicosapentaenoic acid, erucic acid, or docosahexaenoic acid.

Figure 2:
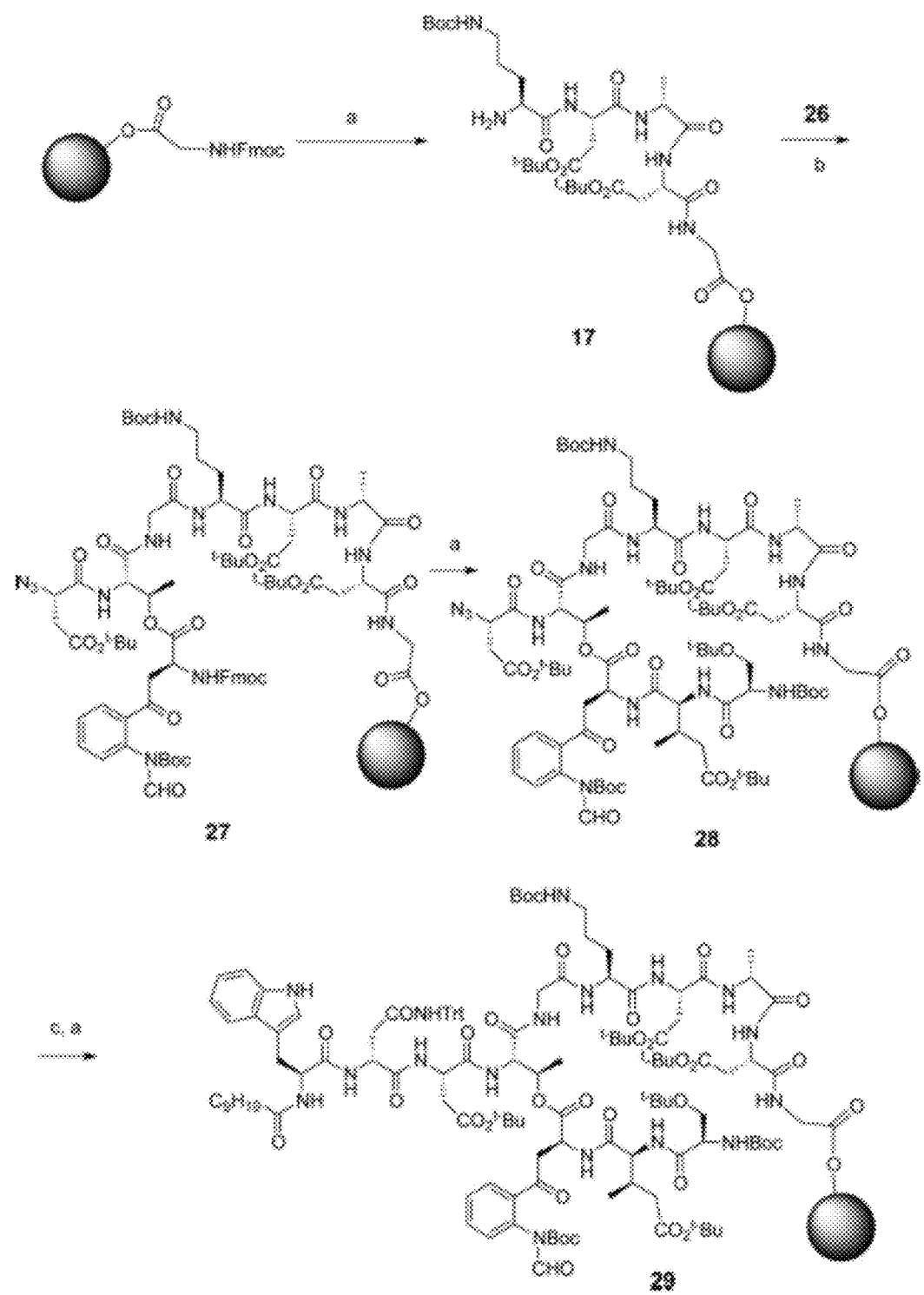
FIG. 2 show a reaction scheme for the preparation of a resin bound linear precursor to daptomycin, according to an embodiment of the invention, where conditions for transformations a through c are: a) Fmoc-SPPS; b) HATU, DIEA, DMF, 45 min; repeat; and c) DTT, DIEA, DMF, 2 h.

In an exemplary embodiment of the invention, as shown in FIG. 2, a preparative method begins with the formation of a resin bound linear precursor for the preparation of daptomycin, a trityl-resin-linked pentapeptide (Fmoc-Orn(Boc)-Asp(tBu)-DAla-Asp(tBu)-Gly) 17, assembled via standard Fmoc-SPPS methods, as can be appreciated by those of ordinary skill in the art. This pentapeptide, is coupled with an azide tetrapeptide including Kyn, N3-Asp(tBu)-Thr-[O-Kyn(Boc,CHO)-Fmoc]-Gly-OH 26, using HATU as the coupling reagent.

Figure 3:
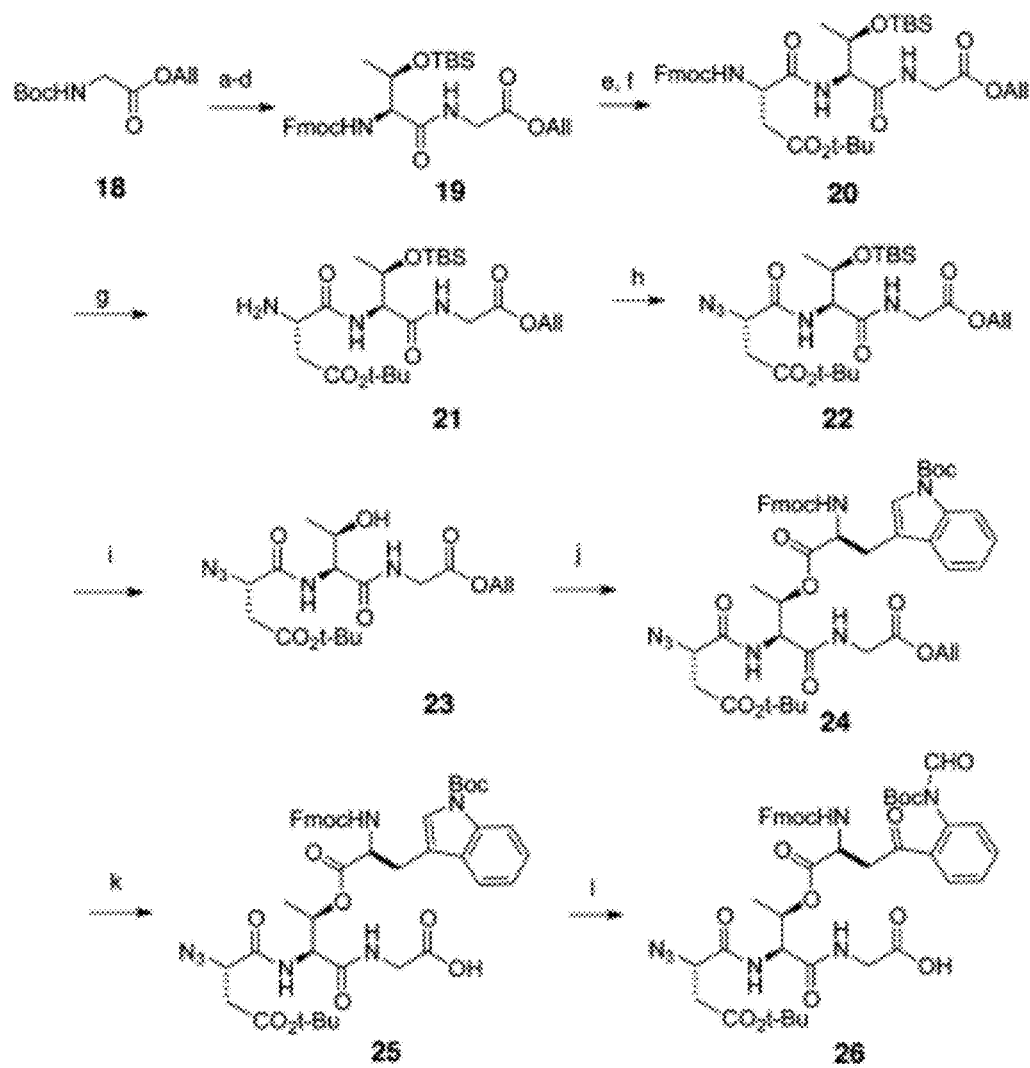
FIG. 3 show a reaction scheme for the preparation of azide terminal Kyn comprising tetramer 26, according to an embodiment of the invention, where conditions for transformations a through 1 are: a) TFA, 30 min; b) Fmoc-Thr (tBu)-OH, EDCI, HOBt, DIEA, $CH_2Cl_2$, 8 h; c) 95% TFA, 30 min; d) TBSCl, imidazole, DMF, 12 h; e) DEA, $CH_2Cl_2$, 2 h, 80%; f) Fmoc-Asp(tBu)-OH, HATU, DIEA, DMF, 8 h; g) DEA, CH2Cl2, 2 h; h) imidazole-1-sulfonyl azide, $CuSO_4 \cdot 5H_2O$, $NaHCO_3$, MeOH, $H_2O$, 2 h; i) TBAF, AcOH, THF, 4 h; j) Fmoc-Trp(Boc)-OH, PyBOP, DIEA, $CH_2Cl_2$, 12 h; k) Pd(PPh$_3$)$_4$, N-methylaniline, THF, 4 h; l) (i) $O_3$, −78° C., $CH_2Cl_2$; (ii) Me$_2$S, −78° C. to rt, 2 h.
Figure 4:
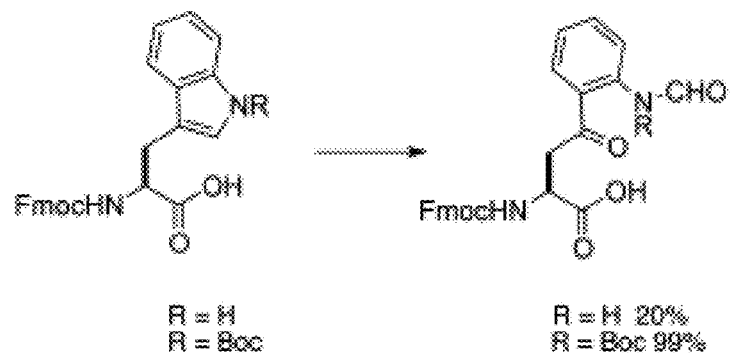
FIG. 4 show a reaction scheme for the ozonolysis of Fmoc-Trp-OH and Fmoc-Trp(Boc)-OH with the indole-N protected with Boc, according to an embodiment of the invention, by the steps of: (i) $O_3$, −78° C., $CH_2Cl_2$, 10 min; and (ii) Me$_2$S, −78° C. then rt, 2 h.

Tetrapeptide, 26, is prepared from the Boc protected allyl ester of glycine 18, as shown in FIG. 3. Acidolysis of the Boc group of 18, followed by coupling with Fmoc-Thr(t-Bu)-OH affords the dipeptide Fmoc-Thr(tBu)-Gly-OAll. Removal of the t-Bu group, followed by silylation of the hydroxyl group yields the dipeptide 19, which, after removal of the N-terminal Fmoc group with DEA, is coupled with Fmoc-Asp(tBu)-OH to form tripeptide 20. Tripeptide 20 undergoes Fmoc removal to amino tripeptide 21, diazo transfer to form 22, and TBS deprotection to give tripeptide 23. Esterification of 23 with Fmoc-Trp(Boc)-OH using PyBOP gives rise to ester 24 without epimerization. Palladium-catalyzed deallylation yields ester 25, which is subjected to ozonolysis to convert Trp to Kyn to yield 26. The conversion of the indole of Fmoc-Trp-OH to the phenylformamide structure of Fmoc-Kyn-OH upon ozonolysis has been reported without protecting the indole nitrogen with disappointing conversions of about 20%. By Boc-protecting the indole N, ozonolysis occurs cleanly, in nearly quantitative yield, as indicated in FIG. 4.

Figure 5:
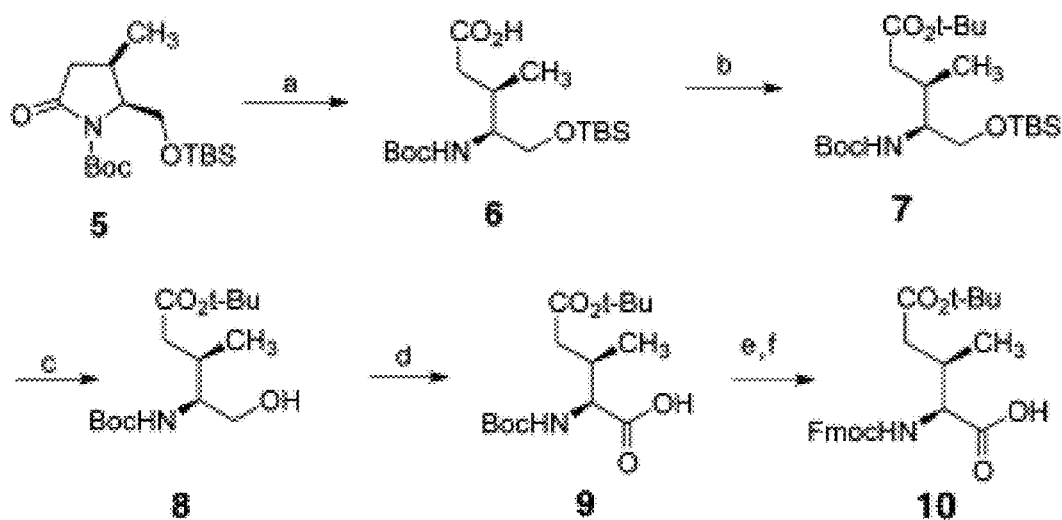
FIG. 5 show a reaction scheme for the preparation of Fmc-3-mGlu-OH 10, according to an embodiment of the invention, where conditions for transformations a through f are: a) LiOH, $H_2O$/THF, 18 h; b) t-Bu-Br, BTEAC, DMAC, $K_2CO_3$, 55° C., 24 h; c) TBAF, THF, 1 h; d) NaIO$_4$, RuCl$_3$, MeCN/CCl$_4$/H$_2$O, 1/1/2, 2 h e) 4 M HCl in dioxane, 0° C. to rt, 50 min; and f) Fmoc-OSu, Na$_2$CO$_3$, dioxane/H$_2$O, 18 h.

The resin-linked peptide 27 from 17 and 26, as shown in FIG. 2, is subsequently coupled with Fmoc-3-mGlu(tBu)-OH 10 and Boc-DSer(tBu)-OH under standard SPPS conditions to produce 28. The preparation of Fmoc-3-mGlu (tBu)-OH 10 from protected cyclic amide 5 is shown in FIG. 5. Ring-opening of 5 with LiOH generated 6, which is subsequent esterified at the γ-carboxylic acid via tert-butyl bromide to yield 7. Subsequent removal of the TBS group with TBAF forms 8, followed by oxidation using sodium periodate and ruthenium(III) chloride to afford Boc-3-mGlu-(tBu)-OH 9. The Boc group of 9 is selectively removed in the presence of the t-butyl ester by treatment with 4 M HCl in dioxane. After protection with an Fmoc group, the desired (2S,3R)-methyl glutamic acid building block 10. As indicated in FIG. 2, after reduction of the N-terminal azide group of 28 using dithiothreitol (DTT), further peptide homologation via Fmoc-SPPS affords the fatty acid terminal side arm of the target linear sequence 29 bound to the resin.

Figure 6:
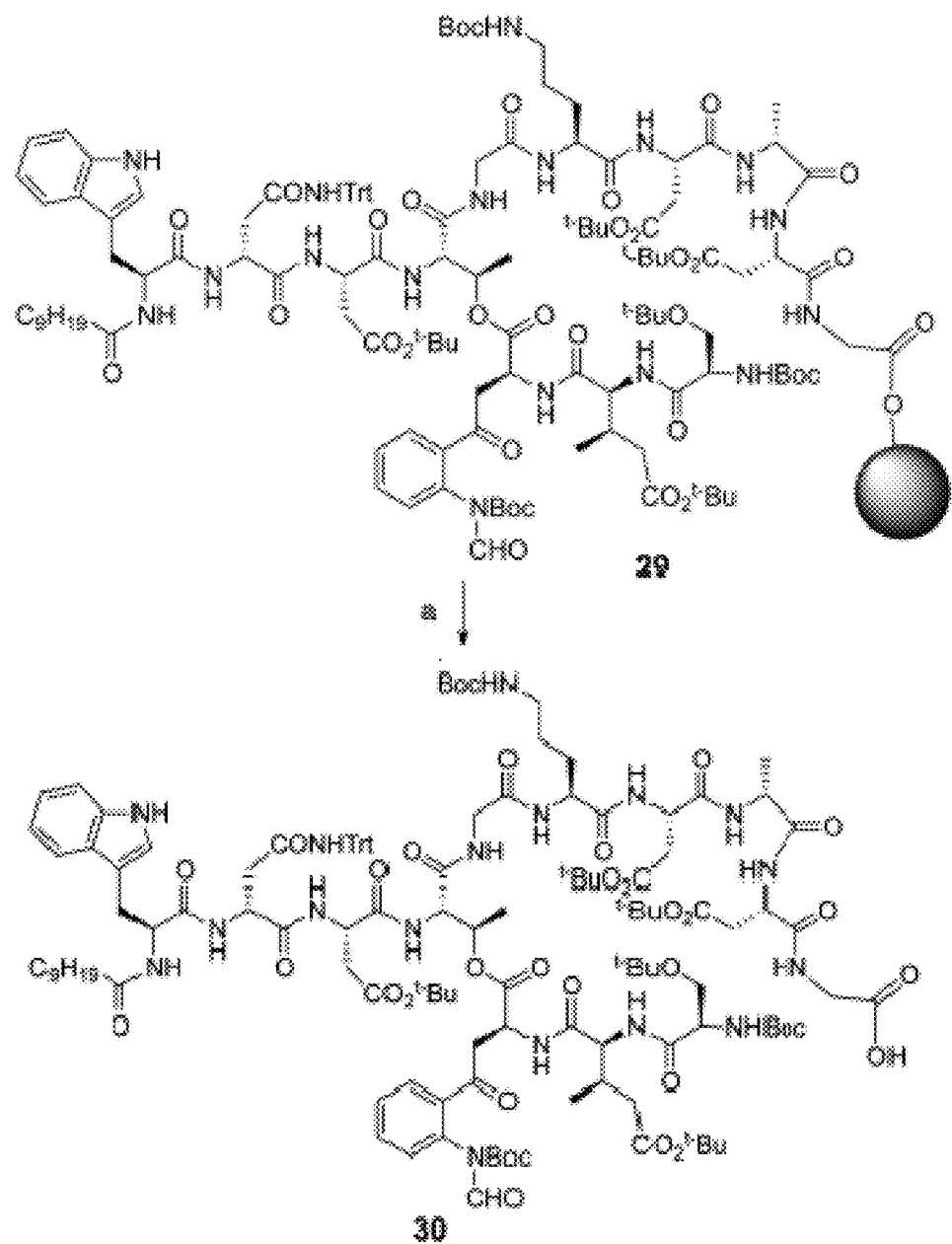
FIG. 6 shows the removal of the linear precursor 30 from the resin, according to an embodiment of the invention, by treatment with AcOH/TFE/DCM for 1.5 h.
Figure 7:
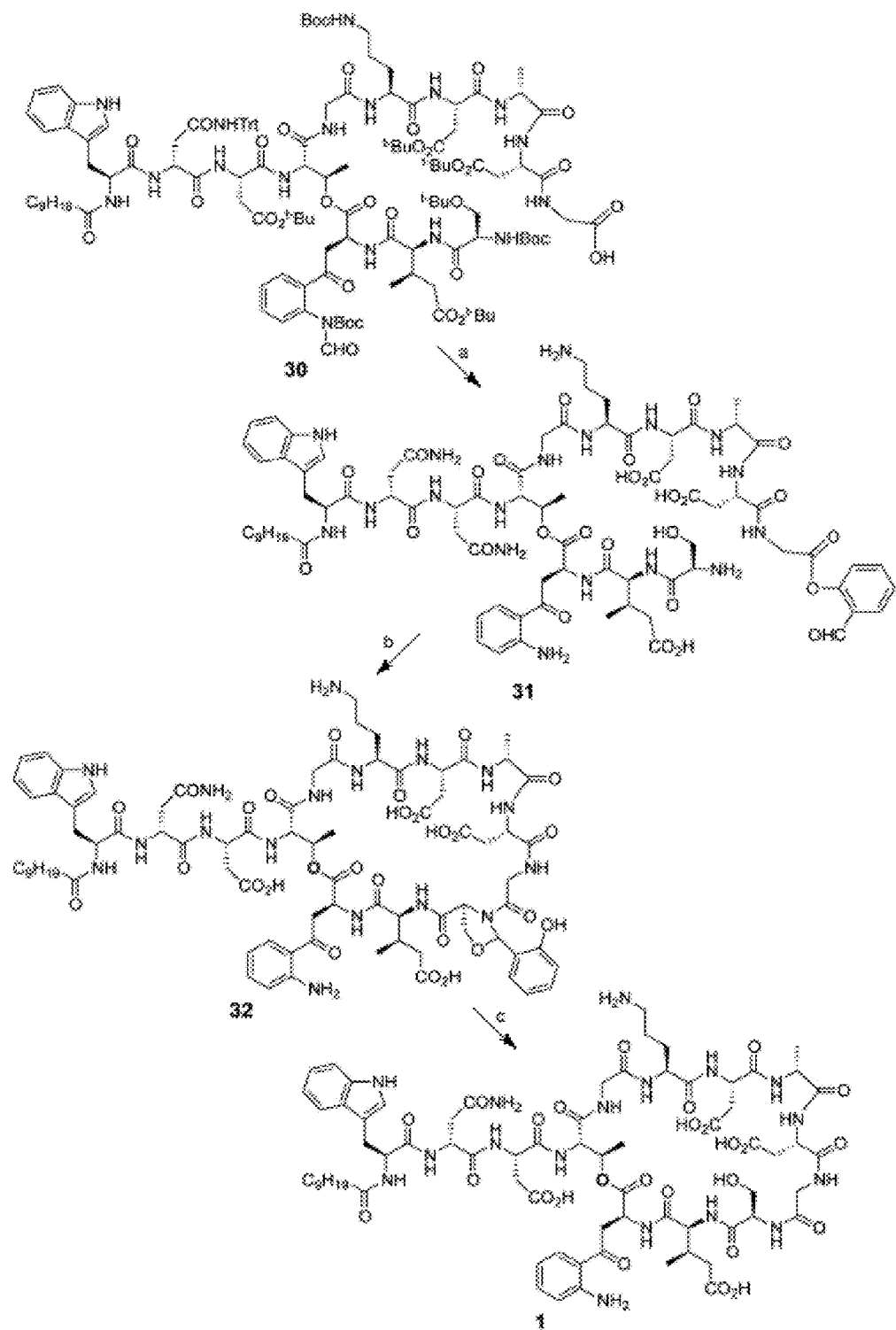
FIG. 7 show a reaction scheme for the macrocyclization of a resin free linear precursor to daptomycin, according to an embodiment of the invention, where conditions for transformations a through c are: a) (i) α,α-dimethoxysalicylaldehyde, PyBOP, DIEA, $CH_2Cl_2$, 2 h; (ii) TFA/$H_2O$/PhOH, 1 h; b) pyridine acetate, rt, 4 h; and c) TFA/H2O, 10 min.

The resin bound 29 is released from the trityl resin to yield the side-chain-protected linear peptide acid 30 using AcOH/TFE/$CH_2Cl_2$, as shown in FIG. 6. FIG. 7 illustrates the conversion of the linear peptide acid 30 to the target exemplary daptomycin 1 in solution. In a first step the C-terminal acid is converted to a salicylaldehyde ester by direct coupling between the peptide acid and α,α-dimethoxysalicylaldehyde. After subsequent deprotection of other protection groups in the linear peptide, salicylaldehyde ester 31 is obtained. The linear side-chain-deprotected peptide salicylaldehyde ester 31 is dissolved in pyridine acetate buffer (mol/mol, 1:1) at a concentration of 5 mM, which results in macrolactamization in effectively quantitative conversion to form a macrocyclic N,O-benzylidene acetal 32. Treatment of acetal 32 yields daptomycin 1 in high yield and can be isolated by semipreparative reverse-phase HPLC in pure form. Surprisingly, the macrocyclization does not require extreme dilutions readily occurring cleanly with 31 concentrations of as little as 5 to more than 50 mM (8.72 to 87.2 g/L) to yield daptomycin 1 as the only product at all concentrations.

Other daptomycin analogues 2 can be assembled by this method, according to embodiments of the invention. Analogues of resin bound pentapeptide precursor 17 can be prepared with the substitution of one or more amino acids, selected from any of the 22 standard α-amino acids or any non-standard α-amino acids for one or more of the amino acids in 17. Analogues of 17 can be tetrapeptides when an amino acid is removed from 17 or hexapeptides when an additional amino acid is included with the amino acids of 17. Analogues of 17 can have formed by substituting amino acids in addition to removing or adding amino acids.

In an embodiment of the invention, the N-terminal azide substituted tetrapetide comprising the protected unnatural amino acid Kynurenine (Kyn) 26, can be replaced with a tetrapeptide that contains the threonine residue to yield an analogue of 27. In an embodiment of the invention, the threonine can be replaced with $H_2NCH(CHRXH)CO_2H$ where X is O, NH, or S, R is H, $CH_3$, $C_2H_5$ $C_3H_7$, or $C_4H_9$. The $H_2NCH(CHRXH)CO_2H$ amino acid substituted for threonine can be serine, R-3-hydroxy-S,2-aminopropanoic acid, R-3-hydroxy-S-2-aminobutanoic acid, R-3-hydroxy-S-2-aminopentanoic acid, cysteine, thiothreonine, R-3-thio-S-2-aminobutanoic acid, R-3-thio-S-2-aminopentanoic acid, S,R-2,3-diaminoproprionic acid, S,R-2,3-diaminobutanoic acid, and S,R-2,3-diaminopentanoic acid. In other embodiments of the invention either or both of the non-Kyn, non-$H_2NCH(CHRXH)CO_2H$ amino acid, and non-serine amino acids can be substituted by and standard or non-standard α-amino acid.

The analogue of 27 is subsequently coupled with Fmoc-3-mGlu(tBu)-OH 10 and Boc-DSer(tBu)-OH under standard SPPS conditions to produce an analogue of 28. The Fmoc-3-mGlu(tBu)-OH can be omitted, substituted with Fmoc-Glu(tBu)-OH, substituted with another Fmoc-amino acid, or an additional amino acid can included before inclusion of the Boc-DSer(tBu)-OH.

The resin bound linear precursor 29 analogue, is completed by the addition of dithiothreitol (DTT) for the reduction of the N-terminal azide group of the 28 analogue. After reduction, the 28 analogue is peptide homologated via Fmoc-SPPS affords with the addition of one to three Fmoc-amino acids and a fatty acid to form the fatty acid amide terminal side arm of resin bound analogue 29. The fatty acid terminal side arm can be that of daptomycin or can have any amino acids substituted for the Trp or Asn or can have either amino acid deleted or an additional amino acid can be included before attachment of the terminal fatty acid. The fatty acid can be enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, or any other $C_7$ to $C_{30}$ fatty acid.

Methods and Materials

All commercial materials (from Aldrich, Fluka and GL Biochem) were used without further purification. All solvents were reagent grade or HPLC grade (from RCI or DUKSAN). Anhydrous tetrahydrofuran (THF) was freshly distilled from sodium and benzophenone. Dry dichloromethane ($CH_2Cl_2$) was distilled from calcium hydride ($CaH_2$). Daptomycin was purchased from Xiang Bo Biotechnology Co., Ltd. All separations involved a mobile phase of 0.05% TFA (v/v) in acetonitrile (solvent A)/0.05% TFA (v/v) in water (Solvent B). HPLC separations were performed with a Waters HPLC system equipped with a photodiode array detector (Waters 2996) using a Vydac 218TPTM C18 column (5 µm, 4.6×250 mm) at a flow rate of 0.6 mL/min for analytical HPLC, Vydac 218TPTM column (10 µm, 10×250 mm) at a flow rate of 4 mL/min for semi-preparative HPLC and Vydac 218TPTM column (10 µm, 22×250 mm) at a flow rate of 10 mL/min for preparative HPLC. Low-resolution mass spectral analyses were performed with a Waters 3100 mass spectrometer. $^1H$ and $^{13}C$ NMR spectra were recorded on Bruker Avance DRX 300 FT-NMR Spectrometer at 300 Hz for $^1H$ NMR and 75.47 MHz for $^{13}C$ NMR, Bruker Avance DRX 400 FT-NMR spectrometer at 400 MHz for 1H NMR and 100 MHz for 13C NMR or Bruker Avance 600 FT-NMR spectrometer at 600 MHz for $^1H$ NMR.

Solid-Phase Peptide Synthesis According to Fmoc-Strategy

Synthesis was performed manually on 2-chlorotrityl chloride Resin (resin loading: 0.4 mmol/g). Peptides were synthesized under standard Fmoc/tBu protocols. The deblock mixture was a mixture of 20/80 (v/v) of piperidine/DMF. The following Fmoc amino acids from GL Biochem were employed: Fmoc-Ala-OH, Fmoc-DAla-OH, Fmoc-Arg (Pbf)-OH, Fmoc-Asn(Trt)-OH, Fmoc-DAsn(Trt)-OH, Fmoc-Asp(tBu)-OH, Fmoc-Glu(tBu)-OH, Fmoc-Gln(Trt)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, Boc-DSer(tBu)-OH.

Upon completion of the synthesis, the peptide resin was subjected to a cleavage cocktail. The resin was filtered and the combined filtrates were blown off under a stream of condensed air. The crude product was triturated with cold diethyl ether to give a white suspension, which was centrifuged and the ether subsequently decanted. The remaining solid was ready for HPLC purification.

Compound 5:

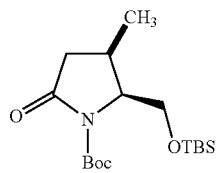 [SMILES: C[C@@H]1CC(=O)N(C(=O)OC(C)(C)C)[C@@H]1CO[Si](C)(C)C(C)(C)C]

Compound 5 was prepared by the method of Milne et al., *J. Am. Chem. Soc.* 2006, 128, 11250-11259.

Compound 6:

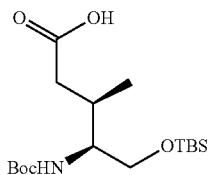 [SMILES: C[C@H](CC(=O)O)[C@@H](CO[Si](C)(C)C(C)(C)C)NC(=O)OC(C)(C)C]

Compound 5 (3.1 g, 9.02 mmol) was dissolved in 50 mL THF and 1 M aqueous LiOH solution (27 mL, 3.0 equiv.) was added to the solution. The reaction mixture was stirred at room temperature for 18 h and concentrated under vacuo. The solution was adjusted to pH=4 with 10% citric acid and extracted with AcOEt (50 mL×3). The combined organic phase was dried over Na$_2$SO$_4$ and concentrated under vacuo to give compound 6 without further purification (3.7 g, 98%).

Compound 7:

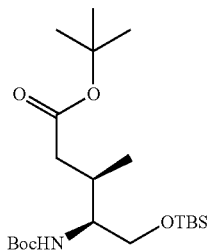

Compound 6 (1.0 g, 2.39 mmol) was dissolved in a solution of benzyltrimethylammonium chloride (546 mg, 2.39 mmol) in 50 mL dimethylacetamide. K$_2$CO$_3$ (9.9 g, 71 mmol) was added to the solution followed by addition of tert-butyl bromide (327 mg, 2.39 mmol). The reaction mixture was stirred at 55° C. for 24 h. The reaction mixture was diluted with AcOEt (100 mL), washed with H$_2$O (50 mL×3) and washed with brine (50 mL×1). The organic phase was dried over Na$_2$SO$_4$, concentrated under vacuo and purified by flash column chromatography on silica gel (hexane/AcOEt, 7:1) to give compound 7 (687 mg, 69%). $^1$H NMR (400 MHz, CDCl$_3$) δ 4.64 (1H, d, J=7.8 Hz), 3.65-3.66 (1H, m), 3.56-3.58 (2H, m), 2.38 (1H, dd, J=4.3 Hz, 14.6 Hz), 2.22-2.28 (1H, m), 2.04 (1H, dd, J=9.2 Hz, 14.5 Hz), 1.43 (18H, s), 0.93 (3H, d, J=6.8 Hz), 0.88 (9H, s), 0.04 (6H, s); $^{13}$C NMR (75 MHz, CDCl$_3$) δ 172.3, 155.8, 80.3, 79.2, 63.3, 55.1, 40.3, 31.9, 28.5, 28.2, 25.9, 18.3, 15.3, −5.3, −5.4; EI-MS [M+] 418.3; HRMS (EI+) calcd. for C$_{17}$H$_{35}$NO$_5$Si [M-t-Bu]+ 361.2284; found 361.2221.

Compound 8:

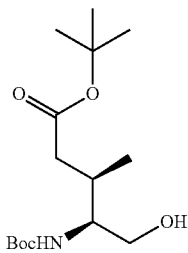 [SMILES: C[C@H](CC(=O)OC(C)(C)C)[C@@H](CO)NC(=O)OC(C)(C)C]

Compound 7 (500 mg, 1.20 mmol) was dissolved in 10 mL THF and a 1M solution of TBAF in THF (6.0 mL, 6.00 mmol) was added to the solution. The reaction mixture was stirred at room temperature for 1 h. The reaction mixture was diluted with AcOEt (50 mL), washed with 1N HCl (25 mL×3) and washed with brine (25 mL×1). The organic phase was dried over Na$_2$SO$_4$, concentrated under vacuo, and purified by flash column chromatography on silica gel (hexane/AcOEt, 4:1) to give compound 8 (305 mg, 84%). $^1$H NMR (400 MHz, CDCl$_3$) δ 4.88 (1H, d, J=7.5 Hz), 3.55-3.62 (2H, m), 3.50-3.54 (1H, m), 2.71 (1H, S), 2.29-2.40 (1H, m), 2.09-2.23 (2H, m), 1.44 (9H, s), 1.43 (9H, s), 0.97 (3H, d, J=6.5 Hz); $^{13}$C NMR (75 MHz, CDCl$_3$) δ 173.0, 156.6, 81.1, 79.7, 63.8, 56.7, 40.1, 31.3, 28.5, 28.2, 16.6; EI-MS [M+] 304.2; HRMS (EI+) calcd. for C$_{14}$H$_{27}$NO$_4$ [M-CH2OH]+ 273.1940; found 273.1927.

Compound 9:

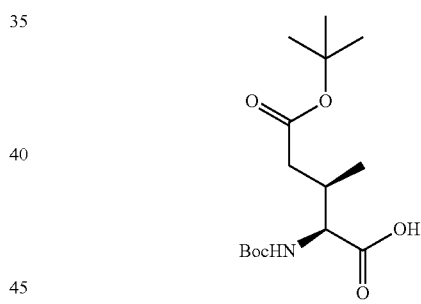

Compound 8 (300 mg, 1.00 mmol) was dissolved in 10 mL of a mixture of CH3CN/CCl$_4$/H$_2$O (1/1/2, v/v/v). NaIO$_4$ (642 mg, 3.00 mmol) was dissolved in the above solution. RuCl$_3$.xH$_2$O (5 mg, cat) was added to the reaction mixture. The reaction mixture was stirred at room temperature for 3 h. The reaction mixture was diluted with CH$_2$Cl$_2$ (50 mL), washed with H$_2$O (25 mL×3) and washed with brine (25 mL×1). The organic phase was dried over Na$_2$SO$_4$, concentrated under vacuo, and purified by flash column chromatography on silica gel (hexane/AcOEt, 1:1, with 1% AcOH) to give compound 9 (260 mg, 82%). $^1$H NMR (400 MHz, CD$_3$OD) δ 6.65 (1H, d, J=9.1 Hz), 4.29 (1H, d, J=4.0 Hz), 2.52-2.55 (1H, m), 2.35 (1H, dd, J=3.6 Hz, 15.8 Hz), 2.09 (1H, dd, J=7.7 Hz, 15.7 Hz), 1.46 (9H, s), 1.45 (9H, s), 0.91 (3H, d, J=6.9 Hz); $^{13}$C NMR (125 MHz, CD$_3$OD) δ 172.1, 170.5, 155.3, 78.9, 77.6, 55.0, 37.4, 30.7, 25.8, 25.4, 12.3; EI-MS [M+] 318.3; HRMS (EI+) calcd. for C$_{11}$H$_{19}$NO$_6$ [M-t-Bu]+ 261.1212; found 261.1205.

Compound 10:

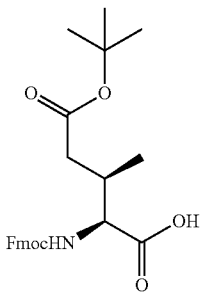

Compound 9 (250 mg, 0.79 mmol) was dissolved in 10 mL 4N HCl in dioxane at 0° C. The reaction mixture was stirred at 0° C. for 30 min and at room temperature for another 20 min. The solvent was removed under a stream of condensed air. The HCl salt was dissolved in 20 mL H$_2$O and Na$_2$CO$_3$ (420 mg, 3.96 mmol) was added to the solution. The resulting solution was added dropwise to a solution of Fmoc-OSu (293 mg, 0.87 mmol) in 10 mL dioxane at 0° C. The reaction mixture was stirred at room temperature for 18 h. The reaction mixture was concentrated under vacuo and adjusted to pH 2 by 1N HCl. The aqueous solution was extracted with Et$_2$O (50 mL×3). The combined organic phase was washed with brine (25 mL×1). The organic phase was dried over Na$_2$SO$_4$, concentrated under vacuo, and purified by flash column chromatography on silica gel (hexane/AcOEt, 2:3, with 1% AcOH) to give compound 10 (187 mg, 54% over 2 steps). $^1$H NMR (400 MHz, CD$_3$OD) δ 7.79 (2H, d, J=7.5 Hz), 7.67-7.70 (2H, m), 7.29-7.40 (4H, m), 4.32-4.41 (3H, m), 4.24 (1H, t, J=6.8 Hz), 2.54-2.61 (1H, m), 2.35 (1H, dd, J=15.8 Hz, 6.8 Hz), 2.10 (1H, dd, J=15.7 Hz, 7.6 Hz) 1.44 (9H, s), 0.94 (3H, d, J=6.8 Hz); $^{13}$C NMR (100 MHz, CD$_3$OD) δ 174.7, 173.3, 158.9, 145.3, 145.2, 142.6, 128.8, 128.2, 126.3, 120.1, 81.8, 68.0, 58.5, 40.3, 33.6, 28.3, 15.2; HRMS (ESI+) calcd. for C$_{25}$H$_{30}$NO$_6$ [M+] 440.1995; found 440.2068.

Kyn-Containing Fragment
Compound 18:

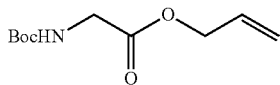

Boc-Gly-OH (5.0 g, 28.56 mmol, 1 equiv.) was dissolved in 20 mL anhydrous CH$_2$Cl$_2$ to which 2-propenol (33.6 g, 56.90 mmol, 20 equiv.), EDCI (9.8 g, 51.04 mmol, 1.8 equiv.), and DMAP (350 mg, 2.86 mmol, 0.1 equiv.) were added. The reaction mixture was stirred at room temperature for 6 h. The reaction mixture was diluted with CH$_2$Cl$_2$ (250 mL), washed with 1N HCl (100 mL×3), and washed with brine (100 mL×1). The organic phase was dried over Na$_2$SO$_4$, concentrated under vacuo, and purified by flash column chromatography on silica gel (hexane/AcOEt, 4:1) to give compound 18 (6.0 g, 98%). $^1$H NMR (300 MHz, CDCl$_3$) δ 5.85-5.98 (1H, m), 5.25-5.37 (2H, m), 5.00 (1H, m), 4.65 (2H, d, J=5.8 Hz), 3.94 (2H, d, J=5.5 Hz), 1.46 (9H, s) $^{13}$C NMR (75 MHz, CDCl$_3$) δ 170.2, 155.8, 131.7, 118.9, 80.1, 65.9, 42.5, 28.4; HRMS (ESI$^+$) calcd. for C$_{10}$H$_{18}$NO$_4$ [M$^+$] 216.1158; found 216.1230.

Compound 19:

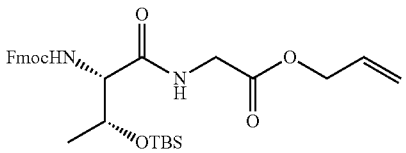

Compound 18 (6.0 g, 27.90 mmol, 1 equiv.) was dissolved in 50 mL TFA. The resulting solution was stirred at room temperature for 30 min to remove the Boc group. TFA was removed under a stream of condensed air leaving a residue of the TFA salt. Fmoc-Thr(tBu)-OH (19.9 g, 50.17 mmol, 1.8 equiv.), EDCI (9.6 g, 50.17 mmol, 1.8 equiv.), HOBt (6.8 g, 50.17 mmol, 1.8 equiv.) and DIEA (20 mL, 111.60 mmol, 4 equiv.) were mixed in 50 mL anhydrous CH$_2$Cl$_2$. The resulting solution was added to the TFA salt. The reaction mixture was stirred at room temperature for 8 h. The reaction mixture was diluted with CH$_2$Cl$_2$ (250 mL), washed with 1N HCl (100 mL×3) and washed with brine (100 mL×1). The organic phase was dried over Na$_2$SO$_4$, concentrated under vacuo, and purified by flash column chromatography on silica gel (hexane/AcOEt, 4:1) to give Fmoc-Thr(tBu)-Gly-OAll (10.2 g, 74%).

Fmoc-Thr(tBu)-Gly-OAll (10.0 g, 20.22 mmol, 1 equiv.) was dissolved in 50 mL 95% TFA. The resulting solution was stirred at room temperature for 30 min to remove the t-Bu group. TFA was removed under a stream of condensed air and the crude compound was dissolved in 50 mL anhydrous DMF. TBSCl (6.2 g, 40.44 mmol, 2 equiv.) and imidazole (4.1 g, 60.66 mmol, 3 equiv.) were added to the DMF solution at 0° C. The reaction mixture was stirred at room temperature for 12 h. The reaction mixture was diluted with AcOEt (250 mL), washed with 1N HCl (100 mL×3), and washed with brine (100 mL×1). The organic phase was dried over Na$_2$SO$_4$, concentrated under vacuo, and purified by flash column chromatography on silica gel (hexane/AcOEt, 4:1) to give compound 19 (7.8 g, 70%). $^1$H NMR (300 MHz, CDCl$_3$) δ 7.76 (2H, d, J=7.5 Hz), 7.59-7.61 (2H, m), 7.29-7.42 (5H, m), 5.84-5.98 (1H, m), 5.82 (1H, d, J=5.9 Hz), 5.25-5.36 (2H, m), 4.66 (2H, d, J=5.6 Hz), 4.38-4.43 (3H, m), 4.12-4.26 (3H, m), 4.02 (1H, dd, J=18.2 Hz, 5.1 Hz), 1.13 (3H, d, J=6.3 Hz), 0.91 (9H, s), 0.14 (6H, s)$^{13}$C NMR (100 MHz, CDCl$_3$) δ 169.9, 169.1, 156.3, 144.0, 143.8, 141.5, 131.6, 127.9, 127.2, 125.3, 120.2, 119.2, 68.2, 67.2, 66.2, 59.5, 47.3, 41.5, 25.9, 18.4, −4.6, −4.9; HRMS (ESI) calcd. For C$_{30}$H$_{41}$N$_2$O$_6$Si [M$^+$] 553.2656; found 553.2728.

Compound 20:

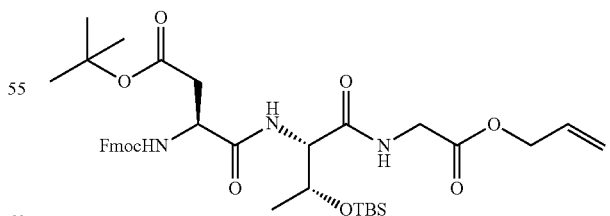

Compound 19 (4.8 g, 8.69 mmol, 1 equiv.) was dissolved in 100 mL of a mixture of CH$_2$Cl$_2$/Diethylamine (2/1 v/v) and stirred at room temperature for 2 h to remove the Fmoc group. The reaction mixture was concentrated under vacuo and purified by flash column chromatography on silica gel (CH$_2$Cl$_2$/MeOH, 20:1) to give the free amine (2.3 g, 80%).

Fmoc-Asp(tBu)-OH (5.7 g, 13.85 mmol, 2.0 equiv.), HATU (4.8 g, 12.62 mmol, 1.8 equiv.) and DIEA (4.9 mL, 28.13 mmol, 4 equiv.) were mixed in 30 mL DMF. The resulting solution was added to the free amine. The reaction mixture was stirred at room temperature for 8 h. The reaction mixture was diluted with CH$_2$Cl$_2$ (250 mL), washed with 1N HCl (100 mL×3) and washed with brine (100 mL×1). The organic phase was dried over Na$_2$SO$_4$, concentrated under vacuo, and purified by flash column chromatography on silica gel (hexane/AcOEt, 2:1) to give compound 7 (3.9 g, 77%). $^1$H NMR (300 MHz, CDCl$_3$) δ 7.76 (2H, d, J=7.4 Hz), 7.58-7.61 (2H, m), 7.28-7.40 (6H, m), 5.84-5.98 (2H, m), 5.26-5.34 (2H, m), 4.62 (2H, d, J=5.6 Hz), 4.46-4.52 (2H, m), 4.34-4.41 (3H, m), 4.23 (1H, t, J=7.0 Hz), 4.12 (1H, dd, J=14.3 Hz, 7.02 Hz), 4.01 (1H, dd, J=18.1 Hz, 5.4 Hz), 2.92 (1H, dd, J=16.7 Hz, 4.6 Hz), 2.75 (1H, dd, J=17.0 Hz, 6.3 Hz), 1.45 (9H, s), 1.13 (3H, d, J=6.3 Hz), 0.89 (9H, s), 0.09 (6H, s)$^{13}$C NMR (100 MHz, CDCl$_3$) δ 171.3, 170.8, 169.9, 169.1, 156.3, 144.0, 143.7, 141.4, 131.7, 127.9, 127.2, 125.2, 120.1, 119.0, 82.2, 67.7, 67.5, 66.0, 58.6, 51.8, 47.2, 41.4, 37.5, 28.1, 25.9, 19.5, 18.0, −4.7, −5.0; HRMS (ESI$^+$) calcd. for C$_{38}$H$_{54}$N$_3$O$_9$Si [M$^+$] 724.3551; found 724.3624.

Compound 21:

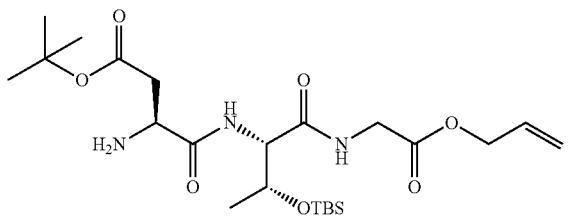 [SMILES: C=CCOC(=O)CNC(=O)[C@@H](NC(=O)[C@@H](N)CC(=O)OC(C)(C)C)[C@@H](C)O[Si](C)(C)C(C)(C)C]

Compound 20 (3.9 g, 5.39 mmol, 1 equiv.) was dissolved in 100 mL of a mixture of CH$_2$Cl$_2$/Diethylamine (2/1 v/v) and stirred at room temperature for 2 h to remove the Fmoc group. The reaction mixture was concentrated under vacuo, and purified by flash column chromatography on silica gel (CH$_2$Cl$_2$/MeOH, 20:1) to give compound 21 (2.8 g, quant.).

Compound 22:

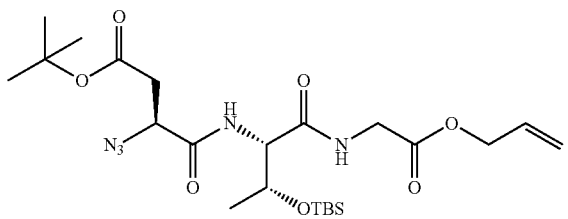 [SMILES: C=CCOC(=O)CNC(=O)[C@@H](NC(=O)[C@H](CC(=O)OC(C)(C)C)N=[N+]=[N-])[C@@H](C)O[Si](C)(C)C(C)(C)C]

Compound 21 (2.8 g, 5.39 mmol, 1 equiv.) was dissolved in 100 mL of a mixture of MeOH and H$_2$O (2:1, v/v). Imidazole-1-sulfonyl azide HCl (2.3 g, 11.02 mmol, 2 equiv.), NaHCO$_3$ (4.5 g, 53.58 mmol, 10 equiv.), and CuSO$_4$.5H$_2$O (13 mg, 0.05 mmol, 0.01 equiv.) were added to the solution and the reaction mixture stirred at room temperature for 12 h. The reaction mixture was concentrated under vacuo, diluted with AcOEt (250 mL), washed with 10% citric acid (100 mL×3), and washed with brine (100 mL×1). The organic phase was dried over Na$_2$SO$_4$ and concentrated under vacuo to give the azido compound 22, which was used in the next step without further purification.

Compound 23:

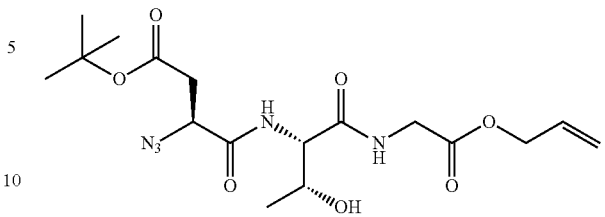

The crude azido compound 22 was dissolved in 50 mL of a 1M TBAF solution in THF and AcOH (1/1, v/v). The reaction mixture was stirred at room temperature for 4 h. The reaction mixture was diluted with AcOEt (250 mL), washed with H$_2$O (100 mL×3), and washed with brine (100 mL×1). The organic phase was dried over Na$_2$SO$_4$, concentrated under vacuo, and purified by flash column chromatography on silica gel (hexane/AcOEt, 1:2) to give compound 23 (1.3 g, 58% over 3 steps). $^1$H NMR (400 MHz, CDCl$_3$) δ 7.38 (1H, d, J=7.7 Hz), 7.18-7.20 (1H, m), 5.86-5.96 (1H, m), 5.26-5.37 (2H, m), 4.64 (2H, dt, J=5.9 Hz, 1.2 Hz), 4.35-4.45 (3H, m), 4.10 (1H, dd, J=17.9 Hz, 5.9 Hz), 4.01 (1H, dd, J=18.0 Hz, 5.6 Hz), 3.46 (1H, d, J=2.7 Hz), 3.07 (1H, dd, J=17.0 Hz, 4.8 Hz), 2.68 (1H, dd, J=17.0 Hz, 8.0 Hz), 1.71 (9H, s), 1.20 (3H, d, J=6.4 Hz)$^{13}$C NMR (100 MHz, CDCl$_3$) δ 171.2, 169.9, 169.8, 169.7, 131.7, 119.5, 82.6, 66.9, 66.5, 60.2, 57.6, 41.6, 38.4, 28.3, 18.5; HRMS (ESI$^+$) calcd. for C$_{17}$H$_{28}$N$_5$O$_7$ [M$^+$] 414.1910; found 414.1983.

Compound 24:

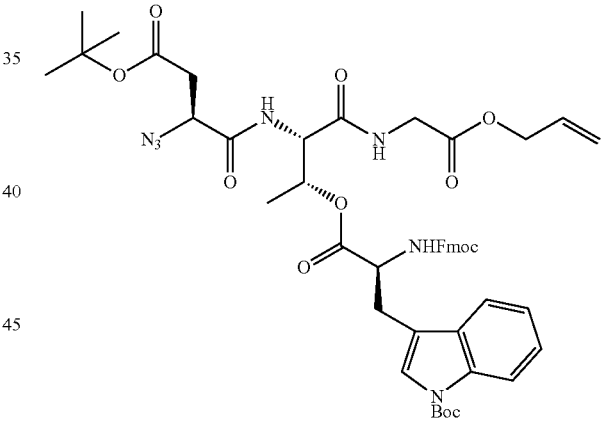

Compound 23 (1.3 g, 3.15 mmol, 1 equiv.), Fmoc-Trp(Boc)-OH (3.6 g, 6.84 mmol, 2.2 equiv.), PyBOP (6.5 g, 12.49 mmol, 4 equiv.), and DIEA (2.2 mL, 12.62 mmol, 4 equiv.) were mixed in 30 mL anhydrous CH$_2$Cl$_2$. The reaction mixture was stirred at room temperature for 12 h. The reaction mixture was diluted with CH$_2$Cl$_2$ (250 mL), washed with 1N HCl (100 mL×3), and washed with brine (100 mL×1). The organic phase was dried over Na$_2$SO$_4$, concentrated under vacuo, and purified by flash column chromatography on silica gel (hexane/AcOEt, 1:1) to give compound 24 (2.5 g, 87%). $^1$H NMR (300 MHz, CDCl$_3$) δ 8.12 (1H, d, J=8.1 Hz), 7.73-7.76 (2H, m), 7.49-7.64 (4H, m), 7.25-7.40 (8H, m), 6.75-6.92 (1H, m), 5.76-5.87 (1H, m), 5.66 (1H, d, J=7.5 Hz), 5.38-5.41 (1H, m), 5.17-5.28 (2H, m), 4.69-4.64 (1H, m), 4.45-4.56 (2H, m), 4.11-4.43 (4H, m), 3.84-4.03 (2H, m), 3.16-3.31 (2H, m), 3.04 (1H, dd, J=16.8 Hz, 4.5 Hz), 2.65 (1H, dd, J=17.0 Hz, 7.9 Hz), 1.64 (9H, s), 1.44 (9H, s), 1.15 (3H, d, J=6.5 Hz)$^{13}$C NMR (100

MHz, CDCl$_3$) δ 170.9, 169.6, 169.3, 168.8, 168.2, 156.3, 149.6, 143.8, 143.7, 141.4, 135.5, 131.5, 130.4, 127.9, 127.2, 125.2, 124.8, 124.5, 122.9, 120.1, 119.1, 119.0. 115.5, 114.9, 84.0, 82.3, 70.3, 67.5, 66.2, 59.9, 55.6, 54.5, 47.2, 41.4, 38.2, 28.3, 28.1, 27.6, 15.4; HRMS (ESI$^+$) calcd. for C$_{48}$H$_{56}$N$_7$O$_{12}$ [M$^+$] 922.3909; found 922.3981.

Compound 25:

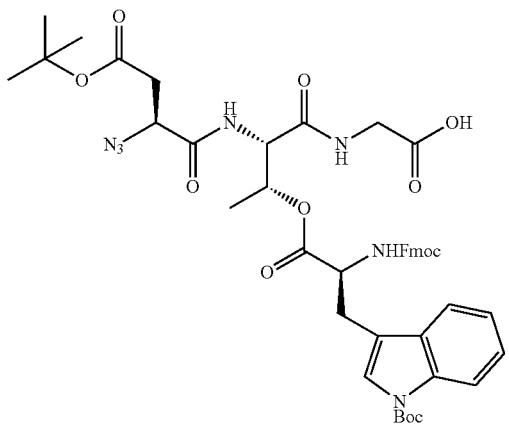

25

Compound 24 (2.5 g, 2.71 mmol, 1 equiv.) and Pd(PPh$_3$)$_4$ (627 mg, 0.54 mmol, 0.2 equiv.) were combined in anhydrous THF under argon. N-methylaniline (3 mL, 28.00 mmol, 10 equiv.) was added under argon to the solution. The reaction mixture was stirred at room temperature under argon for 4 h. The reaction mixture was concentrated under vacuo and purified by flash column chromatography on silica gel (CH$_2$Cl$_2$/MeOH, 20:1, with 1% AcOH) to give the free carboxylic acid, compound 25 (2.1 g, 85%). $^1$H NMR (400 MHz, MeOD) δ 8.07 (1H, d, J=7.9 Hz), 7.72 (2H, d, J=6.5 Hz), 7.60-7.64 (5H, m), 7.48-7.53 (5H, m), 7.11-7.38 (5H, m), 5.40-5.42 (1H, m), 4.67 (1H, d, J=4.4 Hz), 4.60-4.64 (1H, m), 4.38-4.41 (1H, m), 4.30-4.35 (1H, m), 4.07-4.20 (2H, m), 3.88 (2H, br), 3.26 (1H, dd, J=16.0 Hz, 5.8 Hz), 3.11 (1H, dd, J=14.7 Hz, 8.9 Hz), 2.91 (1H, dd, J=16.7 Hz, 5.3 Hz), 2.67 (1H, dd, J=16.7 Hz, 8.3 Hz), 1.54 (9H, s), 1.50 (9H, s), 1.19 (3H, d, J=6.2 Hz)$^{13}$C NMR (100 MHz, MeOD) δ 173.1, 172.4, 171.2, 171.0, 170.7, 158.3, 150.9, 145.1, 142.5, 133.7, 133.7, 133.1, 133.0, 130.0, 129.9, 128.7, 128.1, 126.3, 126.2, 125.5, 125.2, 123.7, 120.9, 120.8, 120.8, 120.1, 116.2, 72.3, 68.1, 60.8, 57.7, 55.6, 42.3, 38.4, 28.3, 28.2, 16.9; HRMS (ESI$^+$) calcd. for C$_{45}$H$_{52}$N$_7$O$_{12}$ [M$^+$] 882.3595; found 882.3668.

Compound 26:

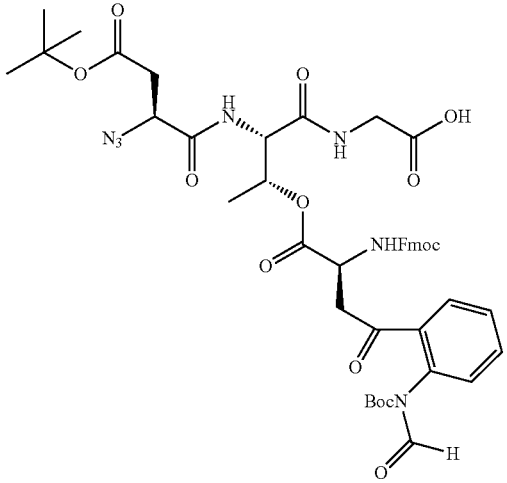

26

The free carboxylic acid, compound 25, (2.1 g, 2.38 mmol, 1 equiv.) was dissolved in 10 mL CH$_2$Cl$_2$ and cooled to −78° C. The resulting solution was treated with O$_3$ at −78° C. for 5 min. Me$_2$S (2 mL, 27.23 mmol, 12 equiv.) was then added at −78° C. The reaction mixture was allowed to warm to room temperature over 2 h. The reaction mixture was concentrated under vacuo and purified by flash column chromatography on silica gel (CH$_2$Cl$_2$/MeOH, 20:1, with 1% AcOH) to give compound 26 as a pair of rotamers (2.0 g, 95%). $^1$H NMR (400 MHz, MeOD) δ 9.24 (1H, s), 8.00 (1H, d, J=6.9 Hz), 7.76-7.79 (3H, m), 7.61-7.66 (9H, m), 7.51-7.56 (5H, m), 7.34-7.38 (3H, m), 7.24-7.34 (4H, m), 5.36-5.40 (1H, m), 4.70-4.74 (1H, m), 4.64-4.67 (1H, m), 4.31-4.40 (3H, m), 4.17-4.22 (1H, m), 3.79-4.00 (2H, br), 3.41-3.69 (2h, M), 2.87-2.91 (1H, m), 2.64-2.70 (1H, m), 1.18-1.41 (18H, m), 0.87-0.91 (3H, m)$^{13}$C NMR (100 MHz, MeOD) δ 171.4, 170.4, 169.8, 169.7, 169.7, 169.6, 169.4, 163.6, 165.9, 151.9, 143.9, 143.8, 141.2, 134.5, 132.8, 132.4, 132.3, 131.8, 131.7, 131.7, 131.6, 131.6, 130.7, 130.6, 129.6, 129.5, 128.9, 128.6, 128.6, 128.5, 127.4, 126.8, 124.9, 119.5, 84.3, 84.2, 81.5, 71.2, 71.1, 66.9, 59.3, 56.3, 56.1, 49.9, 41.8, 41.6, 40.9, 39.0, 37.0, 31.3, 27.1, 26.9, 26.7, 22.3, 19.4, 15.4, 15.3, 13.0; HRMS (ESI$^+$) calcd. for C$_{45}$H'$_{52}$N$_7$O$_{14}$ [M$^+$] 914.3494; found 914.3567.

Construction of Daptomycin Resin Bound Precursors
Compound 17:

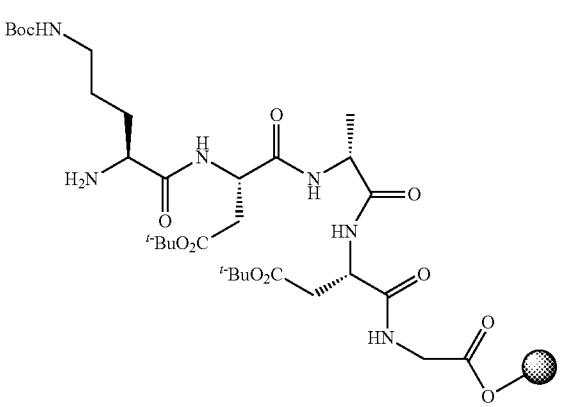

17

Resin bound compound 17 was synthesized from 2-chlorotrityl resin (250 mg, loading: 0.4 mmol/g) using standard Fmoc-SPPS.

Compound 27:

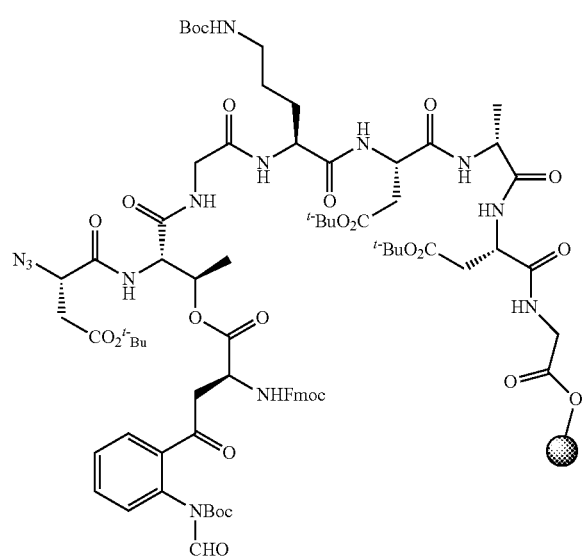

27

Compound 26 (229 mg, 0.25 mmol), HATU (48 mg, 0.25 mmol), DIEA (109 μL, 0.63 mmol) were mixed in 3 mL anhydrous DMF. The resulting solution was added to resin bound 17. The reaction mixture was shaken for 45 min. The solution was removed by filtration and the coupling was repeated to give resin bound 27. The solution was removed by filtration and the resin bound 27 was washed with DMF (5 mL×3).

Compound 28:

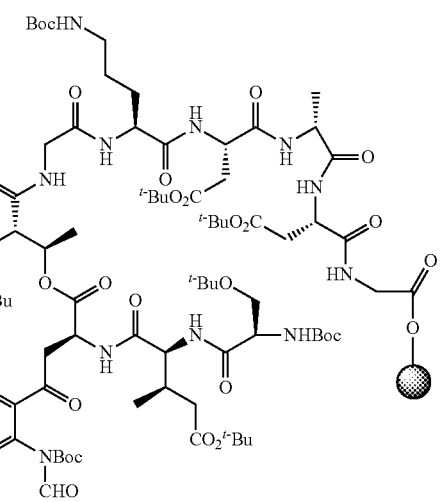

28

Resin bound compound 28 was synthesized using standard Fmoc-SPPS from 27.

Compound 29:

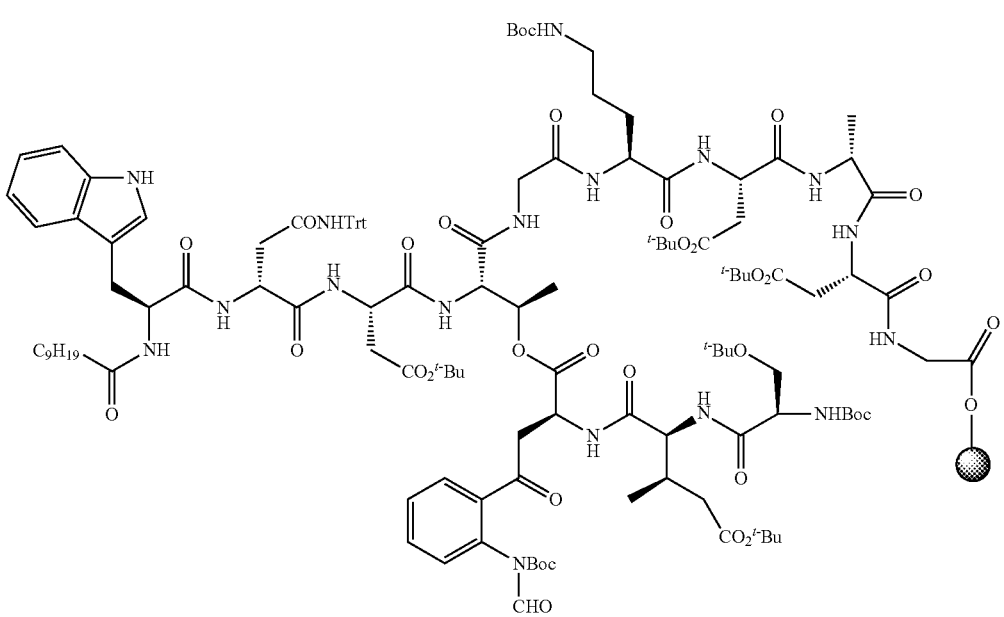

29

A solution of dithiothreitol (2M) and DIEA (1M) in DMF (3 mL) was added to resin bound 28. The reaction mixture was shaken for 2 h to reduce the azido group. The solution was removed by filtration and the resin was washed with DMF (5 mL×3), followed by standard Fmoc-SPPS to give resin bound 29.

Release from the Resin and Cyclization to Daptomycin
Compound 30:

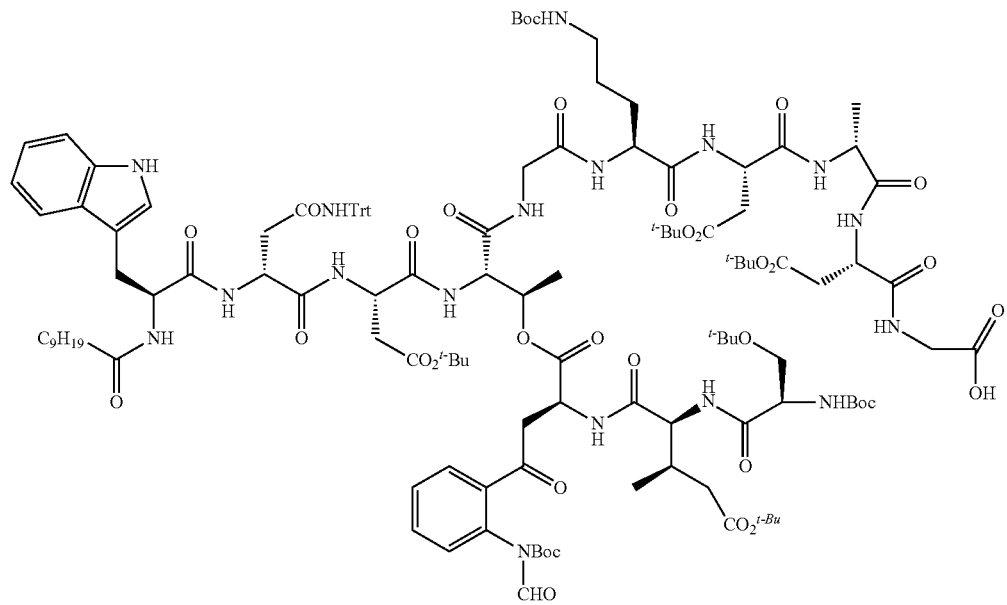

Resin bound 29 was treated with a mixture of TFE/ CH$_2$Cl$_2$/AcOH (1/8/1, v/v/v). The solvent was removed under reduced pressure to release the crude protected peptide 30 from the resin.

Compound 31:

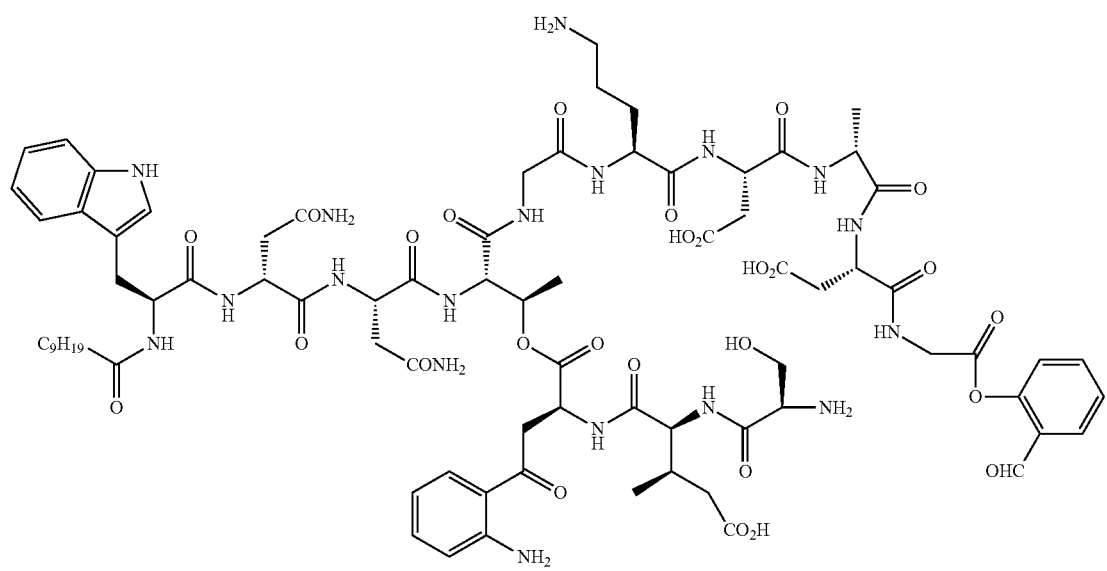

To 50 mg of the crude protected peptide 30 was added α,α-dimethoxy-salicylaldehyde, PyBOP and DIEA in anhydrous CH$_2$Cl$_2$ and treated with TFA/phenol/H$_2$O (95/2.5/2.5, v/v/v). Preparative HPLC purification (20-60% CH$_3$CN/ H$_2$O over 30 min) followed by concentration under vacuo and lyophilization afforded compound 31 as a white powder (5.7 mg, 17%).

Compound 32:

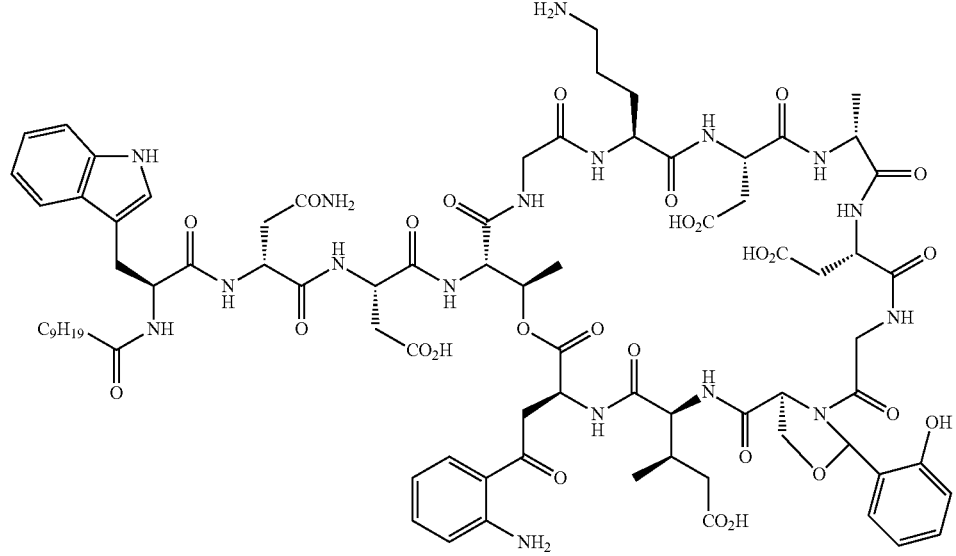

A 0.6 mg portion of compound 31 was dissolved in pyridine/acetic acid (1/1, mole/mole) at a concentration of 5 mM at room temperature. The reaction mixture was stirred at room temperature for 4 h. After completion of the reaction, the solvent was removed by lyophilization to afford the N,O-benzylidene actual intermediate 32. A portion of the N,O-benzylidene acetal intermediate 32 was isolated by semi-preparative HPLC purification and characterized by NMR. The NMR spectrum was recorded at Bruker Avance 600 FT-NMR spectrometer (600 MHz) equipped with a cryoprobe, using water suppression (excitation sculpting). HRMS (ESI+) calcd. for $C_{79}H_{106}N_{17}O_{27}$ [M+] 1724.7444; found 1724.7383.

Compound 1: Daptomycin

Without isolation, the N,O-benzylidene acetal intermediate 32 was treated with TFA/H$_2$O/TIPS (94/5/1, v/v/v) for 10 min. The solvent was removed under a stream of condensed air. Semi-preparative HPLC purification (20-60% CH$_3$CN/ H$_2$O over 30 min) followed by concentration under vacuo and lyophilization afforded compound 1 as a white powder (0.4 mg, 67%). $^1$H NMR was recorded using the same pH condition as disclosed in Qiu et al., *J. Pharm. Sci.* 2011, 100, 4225-4233 and Ball et al., *Org. Biomol. Chem.* 2004, 2, 1872-1878 (5% D$_2$O in pH 7.8 PBS buffer, 0.5 mM). The spectrum was recorded at Bruker Avance 600 FT-NMR spectrometer (600 MHz) equipped with a cryoprobe, using water suppression (excitation sculpting). The $^1$H NMR spectrum obtained was in accordance with the literatures

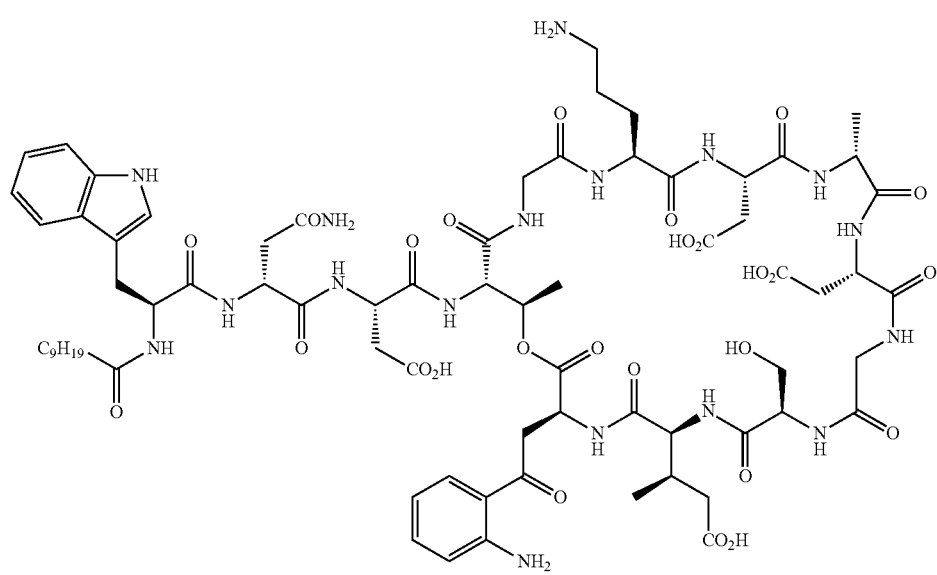

reported and the authentic sample of daptomycin. HRMS (ESI+) calcd. for $C_{72}H_{102}N_{17}O_{26}$ [M+] 1620.7104; found 1620.7176.

All publications referred to or cited herein are incorporated by reference in their entirety, including all figures and tables, to the extent they are not inconsistent with the explicit teachings of this specification. It should be understood that the examples and embodiments described herein are for illustrative purposes only and that various modifications or changes in light thereof will be suggested to persons skilled in the art and are to be included within the spirit and purview of this application.

We claim:

1. A daptomycin analogue, wherein said daptomycin analogue has the structure:

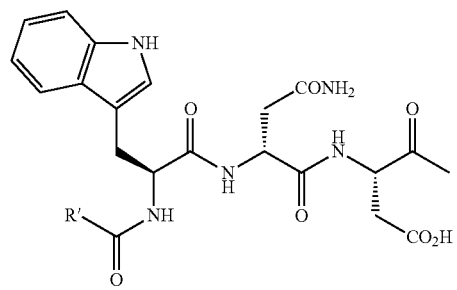

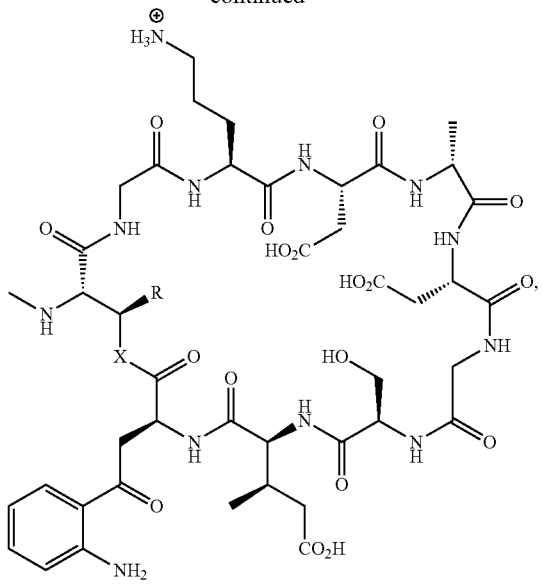

wherein X is O, R is H, and R'C(O)— is a residue of palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, or docosahexaenoic acid.

2. A daptomycin analogue, wherein said daptomycin analogue has the structure:

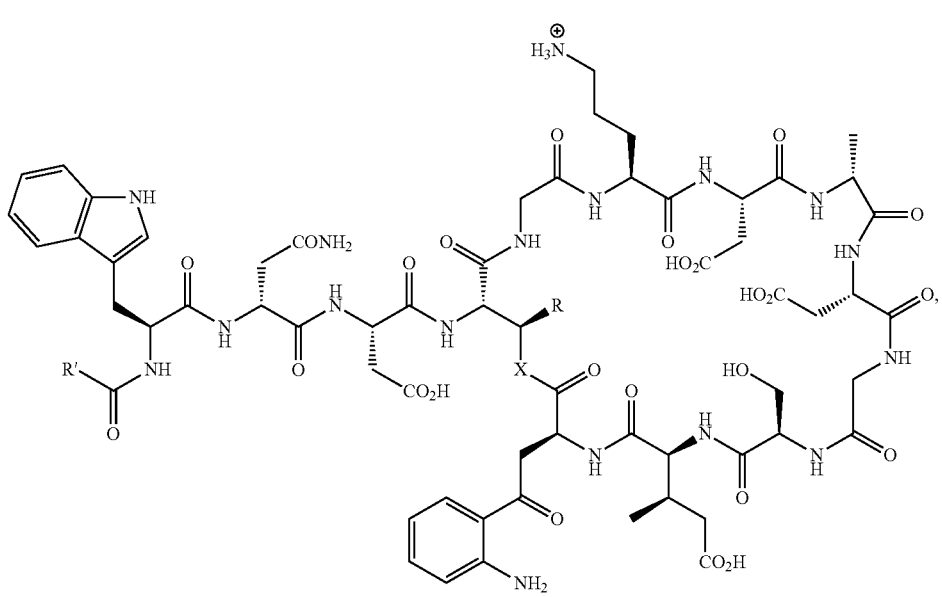

wherein where X is O, and R is H, where R' is a $C_9$ saturated hydrocarbon and wherein said daptomycin analogue has one to four of the amino acid residues other than the $H_2NCH(CHRXH)CO_2H$ amino acid, serine, and kynurenine substituted by any natural or unnatural α-amino acid residue, optionally, has two to four additional amino acid residues in the peptide sequence or macrocyclic ring, or has two to four of the amino acid residues other than the $H_2NCH(CHRXH)CO_2H$ amino acid, serine, and kynurenine removed, and wherein the macrocyclic ring is a 25 to 37 membered ring.

3. A daptomycin analogue according to claim 2, wherein said daptomycin analogue has two to four additional amino acid residues in the peptide sequence or macrocyclic ring.

4. A daptomycin analogue according to claim 2, wherein said daptomycin analogue has other than the $H_2NCH(CHRXH)CO_2H$ amino acid, serine, and kynurenine two to four of the amino acid residues removed.

* * * * *